United States Patent

Watanabe et al.

[11] Patent Number: 4,885,002
[45] Date of Patent: Dec. 5, 1989

[54] BRAIN VENTRICLE SHUNT SYSTEM

[75] Inventors: Yasuo Watanabe, Komae; Kenichi Yamakoshi, Sapporo; Hideaki Shimazu, Tokyo, all of Japan

[73] Assignee: Kabushiki Kaisha Nihon M.D.M., Tokyo, Japan

[21] Appl. No.: 114,192

[22] Filed: Oct. 27, 1987

[30] Foreign Application Priority Data

Nov. 4, 1986 [JP] Japan .................................. 61-262162

[51] Int. Cl.⁴ ............................................. A61M 5/00
[52] U.S. Cl. ......................................... 604/9; 128/748; 73/714; 73/753
[58] Field of Search ...................... 604/8–10, 604/256, 247–249; 128/748; 73/714, 750, 754, 756, 726, 727

[56] References Cited

U.S. PATENT DOCUMENTS

| | | | |
|---|---|---|---|
| 2,862,497 | 12/1958 | Pagano | 604/256 |
| 3,111,125 | 11/1963 | Schulte | 604/9 |
| 3,503,402 | 3/1970 | Schulte | 604/9 |
| 3,595,240 | 7/1971 | Mishler | 604/9 |
| 3,827,439 | 8/1974 | Schulte et al. | 604/9 |
| 3,985,140 | 10/1976 | Harris | 604/9 |
| 4,261,341 | 4/1981 | Hakim et al. | 604/9 |
| 4,314,480 | 2/1982 | Becker | 73/714 |
| 4,605,395 | 8/1986 | Rose et al. | 604/9 |
| 4,621,647 | 11/1986 | Loveland | 73/756 |
| 4,636,194 | 1/1987 | Schulte et al. | 604/9 |
| 4,677,985 | 7/1987 | Bro et al. | 128/748 |
| 4,681,559 | 7/1987 | Hooven | 604/9 |
| 4,723,556 | 2/1980 | Sussman | 128/748 |
| 4,733,566 | 3/1978 | Moriuchi et al. | 73/723 |
| 4,739,771 | 4/1978 | Manwaring | 128/748 |
| 4,781,673 | 11/1978 | Watanabe | 604/247 |

Primary Examiner—C. Fred Rosenbaum
Assistant Examiner—Kathleen A. Daley
Attorney, Agent, or Firm—Bruce L. Adams; Van C. Wilks

[57] ABSTRACT

A brain ventricle shunt system having a first catheter to be inserted into brain ventricle, a second catheter to be inserted into another part of a human body, and a shunt main body connected at one end thereof to the first catheter and at the other end to the second catheter. A check valve is provided for preventing cerebrospinal fluid from flowing back from the second catheter to the first catheter. The shunt main body has a reservoir formed therein and communicated with the first catheter to store the cerebrospinal fluid therein. A dome-shaped flexible portion is formed on the shunt main body and defining the reservoir. The dome-shaped flexible portion is provided to be upwardly projected from the shunt main body by pressure of brain ventricle and provided to be pressed through a scalp by a rod of an external pressure sensor to compress the reservoir.

11 Claims, 10 Drawing Sheets

F I G. 3(a)
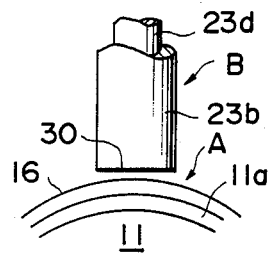
F I G. 3(b)
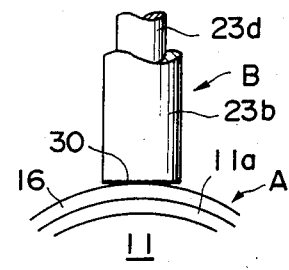
F I G. 3(c)
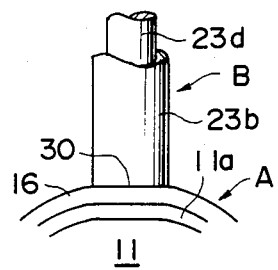
F I G. 3(d)
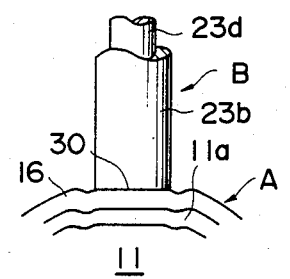

BRAIN VENTRICLE SHUNT SYSTEM

BACKGROUND OF THE INVENTION

The present invention relates to a system for measuring pressure in a brain ventricle of a hydrocephalic patient or the like, and more particularly to a brain ventricle shunt which is implanted in the body of the patient by operation.

Generally, it is necessary to accurately measure pressure in the brain ventricle in order to diagnose cranial nerve trouble.

Heretofore, various measuring means have been proposed. For example, "Remote pressure sensor for a brain ventricle shunt system" is disclosed in "Surg. Neurol" Vol. 11, April, 1979.

As shown in FIGS. 17 and 18, the remote pressure sensor for the brain ventricle shunt system comprises a brain ventricle shunt 50 and a pressure detecting device 60.

The brain ventricle shunt 50 is constructed of a fine tubular brain ventricle catheter 51 to be inserted into the brain ventricle, a shunt main body 52 connected to the brain ventricle 51 and including a reservoir and a pump chamber, and a tubular peritoneum or auricle catheter 53 connected to the shunt main body and to be inserted into the peritoneum or the auricle.

As shown in FIG. 18, the shunt main body 52 is implanted on a skull 17 under a scalp 16. Inside the shunt main body, there is provided a relief valve 54 composed of a miter valve or the like, which is closed and opened by means of the pressure of the cerebrospinal fluid, which is an excrement fluid from the brain ventricle. A flexible diaphragm 55 is formed on an upper portion of the main body 52 to be upwardly expanded by the pressure of the cerebrospinal fluid passing through the chamber under the diaphragm. A stopper 56 is provided on a lower portion of the chamber, corresponding to the diaphragm 55.

A pressure sensor 57 of the pressure detecting device 60 is embedded in the main body 52 at a lower portion thereof. The sensor 57 comprises a tuning circuit 58 having a resonator such as a coil embedded in the main body 52, and a tuning element 59 provided on a wall forming diaphragm 55 for changing the resonance frequency in accordance with the distance from the tuning circuit 58.

The pressure detecting device 60 has other elements disposed outside the body of the patient. That is, there are provided an antenna 61 for transmitting electromagnetic waves to the pressure sensor 57 for detecting the resonance frequency thereof, and an indicator 62 for indicating the resonance frequency of a signal supplied to the antenna 61. A non-metallic pressure applying member 63 is disposed between the scalp 16 and the antenna 61. The member 63 is supplied with compressed air from a compressed air supply device 64. When the member 63 is expanded by the compressed air, the tuning element 59 is moved closer to the tuning circuit 58. Further, a pressure guage 65 for detecting the pressure of the compressed air is provided in the device 60.

Describing the measuring operation.

(1) The antenna 61 is disposed at a detecting position. The diaphragm 55 is pressed by a finger through the scalp 16 to cause the tuning element 59 to approach the tuning circuit 58. The indicator 62 receives a signal from the antenna 61 and the calibration of the indicator is performed.

(2) When the finger is removed, it is confirmed that the diaphragm 55 is outwardly expanded to separate the tuning element 59 from the tuning circuit 58, and that the indication of indicator 62 is away from the calibration range.

(3) The pressure applying member 63 is inserted between the scalp 16 and the antenna 61 and expanded to press the diaphragm 55. At the time the indicator 62 indicates the calibration range, the pressure on the pressure guage 65 corresponds to the pressure in the brain ventricle.

However, the tuning circuit 58 and the tuning element 59 in the head have influence on electromagnetic waves radiated from a scanner such as the CT scanner and neuclear magnetic resonance scanner. Accordingly, these elements interfere with the forming of a tomogram by such a scanner. Further, the structure of the system is complicated, and it is difficult to perform the calibration with accuracy.

SUMMARY OF THE INVENTION

The object of the present invention is to provide a system for measuring pressure in a brain ventricle which is simple in construction and easy in operation, thereby eliminating the above described disadvantages of the conventional system.

According to the present invention, there is provided a brain ventricle shunt system having a first catheter to be inserted at a tip portion thereof into a brain ventricle of a human body so as to drain cerebrospinal fluid from the brain ventricle, a second catheter to be inserted at a tip portion thereof into another part of the human body so as to feed the cerebrospinal fluid into the part, and a shunt main body connected at one end thereof to the first catheter and at the other end to the second catheter so as to fluidically communicate the first and second catheters with each other, and a check valve for preventing the cerebrospinal fluid from flowing back from the second catheter to the first catheter.

The shunt main body has a reservoir formed therein to communicate with the first catheter to store the cerebrospinal fluid therein, and a dome-shaped flexible portion is formed on the shunt main body and defines the reservoir. The dome-shaped flexible portion is configured to be upwardly projected from the shunt main body by the pressure of the brain ventricle and configured to be pressed through the scalp by a rod of an external pressure sensor to compress the reservoir.

In an aspect of the invention, a shut-off valve is provided in a flow passage formed in the shunt main body between the reservoir and the second catheter, for shutting off flow of the cerebrospinal fluid from the reservoir to the second catheter.

The shut-off valve means comprises a spherical valve plug, a valve seat formed in the flow passage in the shunt main body for receiving the valve plug in closed state of the valve means and, a valve chamber provided adjacent the valve seat for receiving the valve plug in the open state of the valve means.

In a further aspect of the present invention, the shut-off valve means comprises a cavity provided in the flow passage so as to be communicated with the reservoir and with the flow passage through an opening, a flexible wall defining an upper portion of the cavity, and a plug formed on an underside of the flexible wall so as to be engaged with the opening to close it when the flexible wall is pressed to compress the cavity, and the shunt main body has means for disengaging the plug from the opening.

The shut-off valve means may be composed of a pair of parallel shut-off valves, whereby the flow rate of cerebrospinal fluid can be changed.

Various general and specific objects and advantages of the invention will become apparent when reference is made to the following detailed description of the invention considered in conjunction with the accompanying drawings.

BRIEF DESCRIPTION OF THE DRAWINGS

FIGS. 3(a) to 3(d) are elevational views showing relationships between a sensor end and a dome of a shunt main body;

DETAILED DESCRIPTION OF THE PREFERRED EMBODIMENTS

Figure 1:
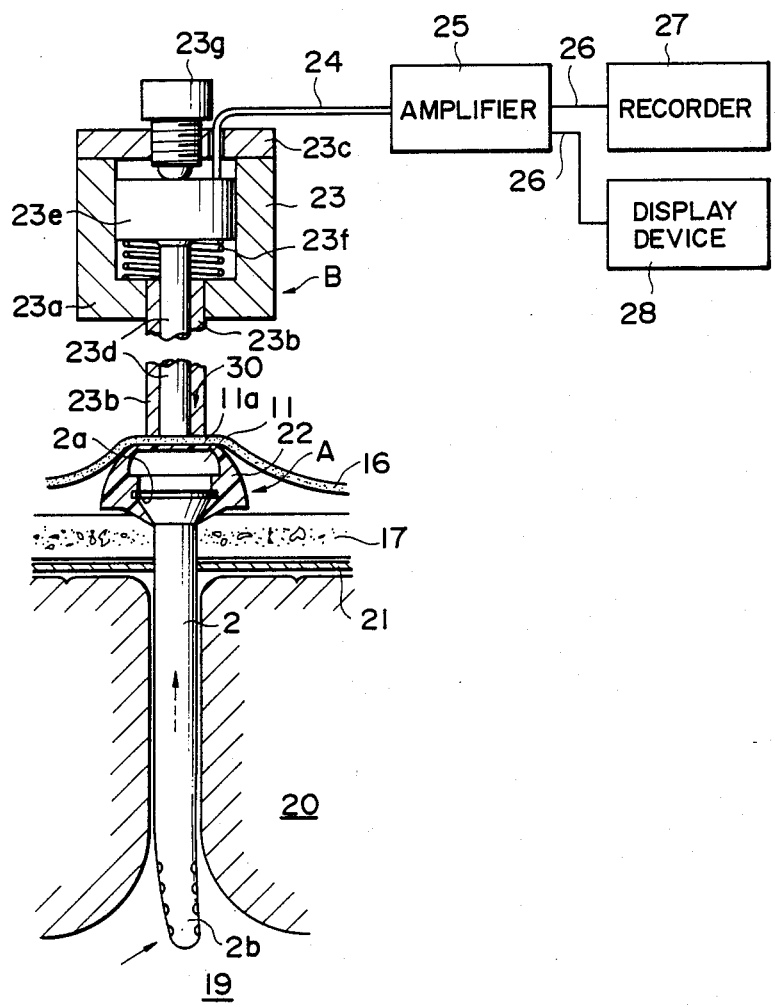
FIG. 1 is a sectional view of a shunt system used for measuring pressure in a brain ventricle, according to the present invention.

Referring to FIGS. 1 to 6, and particularly to FIG. 1, a system for measuring pressure in a brain ventricle according to the present invention consists of a brain ventricle shunt A implanted in a head of a patient and a pressure detecting device B provided outside of the body of the patient. The device B is disposed near the patient such that a sensing portion of the device contacts a top of the brain ventricle shunt A through the patient's scalp 16.

The brain ventricle shunt A comprises a fine tubular brain ventricle catheter 2 inserted into a brain ventricle 19 of the patient at a tip portion 2b thereof to drain cerebrospinal fluid from the brain ventricle 19, and a shunt main body 22 having a reservoir 11 therein. The main body is made of silicone resin or the like and connected to the catheter 2 at a base portion 2a thereof. The shunt main body 22 has a dome-shaped or arcuate flexible portion 11a defining the reservoir 11 and forming an upper wall of the reservoir. The reservoir 11 is communicated with the brain ventricle 19 through the catheter 2.

The pressure detecting device B comprises a pressure detector 23 having a pressure sensor 23e, an amplifier 25 connected to the sensor 23e for receiving a pressure detecting signal through a lead 24 and amplifying the signal, and a recorder 27 such as a printer and a display device 28 such as a CRT connected to the amplifier 25 through a lead 26, respectively.

The pressure detector 23 comprises a casing 23a, an external guide pipe 23b secured to the casing 23a and having a predetermined length, a cover 23c secured to a back of the casing, and a pressure receiving rod 23d slidably mounted in the pipe 23b, an end of which is connected to the pressure sensor 23e. The pressure sensor (or load sensor) 23e comprises a semiconductor pressure sensor coated with silicone operates to convert the pressure from the rod 23d into an electric signal. The pressure detector 23 further has a spring 23f mounted on the rod 23d between the casing 23a and the sensor 23e to urge the sensor into engagement with a zero adjuster 23g threaded in the cover 23c, for positioning the sensor 23e. A sensor end 30 is disposed at a position substantially coplanar with the underside of pipe 23b.

Reference numeral 20 designates a brain and 21 is a dura mater.

The measuring operation of the pressure in the brain ventricle will be described with reference to FIGS. 2 to 4.

(1) Cerebrospinal fluid is fed through the brain ventricle catheter 2 to the reservoir 11 implanted on the skull 17 under the scalp 16. The dome-shaped flexible portion 11a on the reservoir 11 is outwardly protruded by the pressure of cerebrospinal fluid (step a2 of FIG. 2).

(2) The pressure detecting device B is turned on. The measuring operation is started. As shown in FIG. 3(a) which corresponds to a depth LA of a sensor end at a time tA in FIG. 4, the sensor end 30 is positioned apart from the scalp 16 to be in a non-contact state therewith. Thus, the dome 11a is not pressed by the external force.

Figure 4:
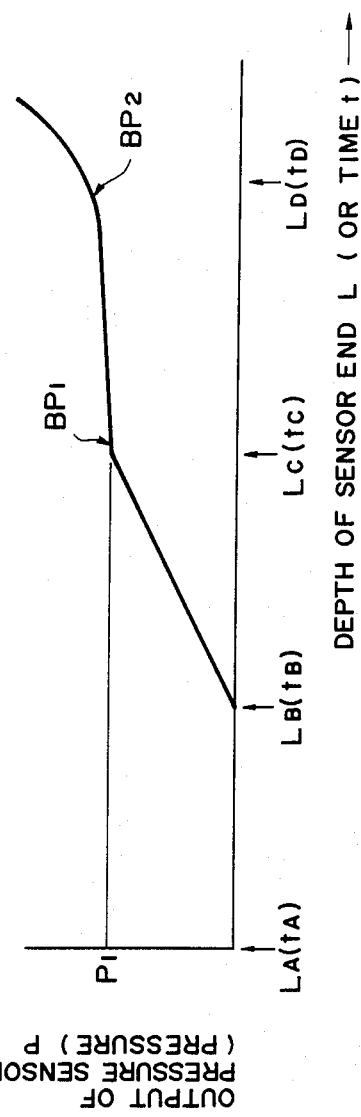
FIG. 4 is a graph showing a characteristic of pressure measuring operations.

(3) The casing 23a is lowered to displaced and press the sensor end 30 against the dome 11a through the scalp 16, as shown in FIG. 3(b) which corresponds to a depth LB of the sensor end 30 at time tB in FIG. 4 (step a3).

(4) The sensor end 30 is further lowered until an upper central portion of the dome 11a becomes flat (see FIG. 3(c) which corresponds to a depth LC at a time tC of FIG. 4). In such a state, surfaces of the sensor rod 23b and the upper portion of the dome 11a become co-planar. Thereafter, as shown in FIG. 4, a curve representing the relationship between depth L and pressure P changes at a point (hereinafter called curve changing point BP₁).

(5) The sensor end 30 is further lowered a predetermined extent until the upper portion of the dome 11a is dented (FIG. 3(d)) which corresponds to a depth LD at a time tD in FIG. 4). At this point, the end of the sensor rod 23d begins to indent the dome 11a. The curve representing the relationship between the depth L and the pressure P changes at a point (called curve changing point $BP_2$).

(6) The pressure P measured by the detecting device B is recorded by the recorder 27 and displayed by the display device 28, and the range between $BP_1$ and $BP_2$, where the pressure P does not change or slightly increases even if the depth of the sensor end 30 changes, is found out on the display. The pressure in the unchanged range is regarded as the pressure in the brain ventricle (step a4).

The principle of the present invention is established under the following condition and effective on the following object.

The condition is that the pressure existing in the flexible dome 11a having a radius r is equal to the pressure in the brain ventricle. Namely, it is necessary that the pressure in the brain ventricle does not change, if the dome 11a is indented.

The measuring object is the pressure in the shunt main body 22 installed under the scalp 16.

The principle may be explained by the Laplace theorem as described hereinafter.

Figure 5:
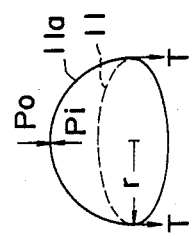
FIG. 5 is a schematic perspective view of a reservoir of the present invention for explaining the operations.

As shown in FIG. 5, assuming that the dome 11a is a part of a sphere having radius r, the Laplace theorem may be expressed as follows.

$Pi - Po = 2T/r$ where
 $Pi$ is inside pressure (brain ventricle pressure),
 $Po$ is outside pressure (ordinarily the atmospheric pressure),
 $T$ is tension of the dome (including scalp).

If the condition that Pi is equal to Po is established, the inside pressure Pi can be measured from the outside of the dome 11a. Further, a following measuring principle may be described from the Laplace theorem.

Figure 6:
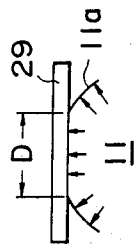
FIG. 6 is a side view of the reservoir for explaining the operations.

As shown in FIG. 6, when the dome 11a is pressed by a plate 29, a flat top surface D is formed on the dome. In the range of the surface D, the radius r is regarded as becoming infinite in accordance with the above Laplace theorem. If the radius r is infinity ($\infty$), the right side of the above equation becomes zero, thereby establishing Pi=Po. In other words, it is proved that the outside pressure applied to the dome to form a flat top surface thereon is equal to the inside pressure.

In practice, attention must be directed to following matters.

1. Pressing the dome 11a to form a flat top surface.
2. Measure the outside force only in the range D.
3. Do not excessively press the dome.

FIGS. 7 to 14 show a second embodiment of the present invention. The device for measuring brain ventricle pressure of the second embodiment is different from the first embodiment, but the pressure detecting device B of the first embodiment is used.

A brain ventricle shunt A' of the second embodiment comprises a fine tubular brain ventricle catheter 2 to be inserted at a tip portion thereof into the brain ventricle of a patient so as to drain cerebrospinal fluid from the brain ventricle, a peritoneum or auricle catheter (hereinafter called peritoneum catheter) 3 which defines a discharge flow passage and which is to be inserted at a tip portion thereof into the peritoneum or the auricle of the patient so as to feed the cerebrospinal fluid into the peritoneum or the auricle, and a shunt main body 1 which is provided with a main flow passage 10 fluidically interconnecting a base portion 2a of the brain ventricle catheter 2 and a base portion 3a of the peritoneum catheter 3 so as to provide fluidic communication between both catheters 2, 3. The shunt main body 1 is formed so as to have soft walls from a suitable silicone resin or the like.

The shunt main body 1 is provided with a pair of check valves 4 which operate to prevent cerebrospinal fluid from flowing back from the peritoneum catheter 3 to the brain ventricle catheter 2. In this embodiment, a slit-type relief valve 6 (7) is employed as the check valve 4. Both the relief valves 6, 7 are arranged to serve also as flow-rate regulators, for a flow-rate switching mechanism 5, which will be described below.

Figure 14:
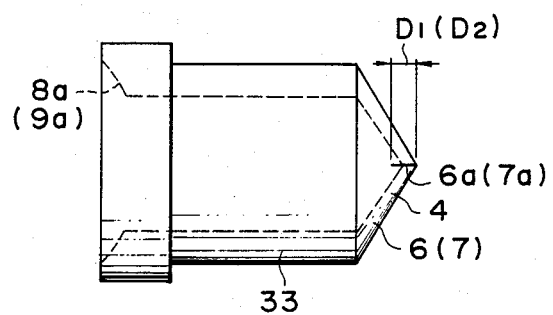
FIG. 14 is an enlarged plan view showing a relief valve member.

These slit-type relief valves 6, 7 are formed with valve seats 8a, 9a, respectively as shown in FIG. 14, thereby forming a relief valve member 33. The relief valve member 33 is bonded to the main body 1 in such a way that it is held between upper and lower parts 1A, 1B of the shunt main body 1.

The shunt main body 1 is fixed on the skull 17 under the scalp 16 by stitching the scalp 16 with a suture which extends through a suture through-hole 15.

The shunt main body 1 is further provided with a reservoir 11 having a spherical dome 11a formed above the brain ventricle catheter 2 so as to fluidically interconnect passage 10 and catheter 2, a small compartment 12' formed in the shunt main body 1 on the side of the peritoneum catheter 3 so as to fluidically interconnect passage 10 and catheter 3, and first and second branch flow passages 13, 14 extending in opposite direction with respect to each other and upon opposite sides of the main flow passage 10 so as to fluidically interconnect the peritoneum catheter end 10a of main flow passage 10 and the small compartment 12' with each other.

As described above, the first branch flow passage 13 is provided with slit-type relief valve 6 so as to define a first flow-rate regulator. As shown in FIG. 14, relief valve 6 has a slit 6a of a predetermined depth $D_1$ for controlling the flow rate to a predetermined flow rate $Q_1$ when the first flow passage 13 is in a communicating state. A ball-type ON-OFF valve 8 is provided to shut off the first flow passage 13 upon reception of a driving force from the outside of the shunt main body 1.

The ball-type ON-OFF valve 8 has a first hemispherical valve seat 8a formed in a wall of the shunt main body 1, a valve chamber 8b extending longitudinally in the first flow passage 13, a spherical valve plug 8c provided in the valve chamber 8b and movable upon reception of an external driving force, such as, for example, a finger 18, the force of which may be applied through the soft upper and front walls 1a, 1b of the valve chamber 8b and the scalp 16, a second hemispherical valve seat 8d for holding the valve plug 8c at a closed position for allowing the valve plug 8c to seat thereon whereby the valve plug 8c is held between the hemispherical seat 8d and the soft upper wall 1a at a position registered with the valve seat 8a so as to close the ON-OFF valve 8 and to shut off the first flow passage 13, and a third hemispherical valve seat 8e for holding the valve plug 8c at an opened position for allowing the valve plug 8c to seat thereon whereby the valve plug 8c is held between the hemispherical seat 8e and the soft upper wall 1a at a position remote from the valve seat 8a so as to open the ON-OFF valve 8 and to permit communication on the first flow passage 13 with the small compartment 12'.

The second flow passage 14 is provided with slit-type relief valve 7 so as to define a second flow-rate regulator. As shown in FIG. 14, relief valve 7 has a slit 7a of a predetermined depth $D_2(<D_1)$ for controlling the flow rate to a predetermined flow rate $Q_2$ (in the illustrated embodiment, $Q_2 = 1/2Q_1$) when the second flow passage 14 is in a communicating state. A ball-type ON-OFF valve 9 is provided to shut off the second flow passage 14 upon reception of a driving force from the outside of the shunt main body 1.

The ball-type ON-OFF valve 9 is constructed of a hemispherical valve seat 9a formed in a wall of the shunt main body 1, a valve chamber 9b extending longitudinally in the second flow passage 14, a moveable spherical valve plug 9c provided in the valve chamber 9b and movable upon reception of an external driving force, such as, for example, the finger 18, the force of which may be applied through the soft upper and front walls 1a and 1c of the valve chamber 9b and the scalp 16, a closed position holding hemispherical valve seat 9d for allowing the valve plug 9c to seat thereon whereby the valve plug 9c is held between the hemispherical seat 9d and the soft upper wall 1a at a position registered with the valve seat 9a so as to close the ON-OFF valve 9 and to shut off the second flow passage 14, and an opened position holding hemispherical seat 9e for allowing the valve plug 9c to seat thereon whereby the valve plug 9c is held between the hemispherical seat 9e and the soft upper wall 1a at a position remote from the valve seat 9a so as to open the ON-OFF valve 9 and to permit communication of the second flow passage 14 with the small compartment 12'. Namely, the ball-type ON-OFF valve 9 is constructed substantially in the same manner as the above-described ball-type ON-OFF valve 8.

The first relief valve 6 has a regulated flow rate greater than that of the second relief valve 7. In the present embodiment, the relief valves 6, 7 are both constructed as single slit-type check valves. They may however be replaced by cruciform-slit-type, spring-type or membrane-type check valves.

As the material for the movable ball-type valve plugs 8c, 9c, a plastic or metallic material may be used. It is also possible to use a metal ball with a silicone coating applied thereon. In the case of plastic movable spherical valve plugs, it is desirable to mix a contrast medium with the plastic material so as to permit determination of the positions of the movable spherical valve plugs 8c, 9c by means of an X-ray picture in the same manner as in the case of metal movable spherical valve plugs.

Figure 7:
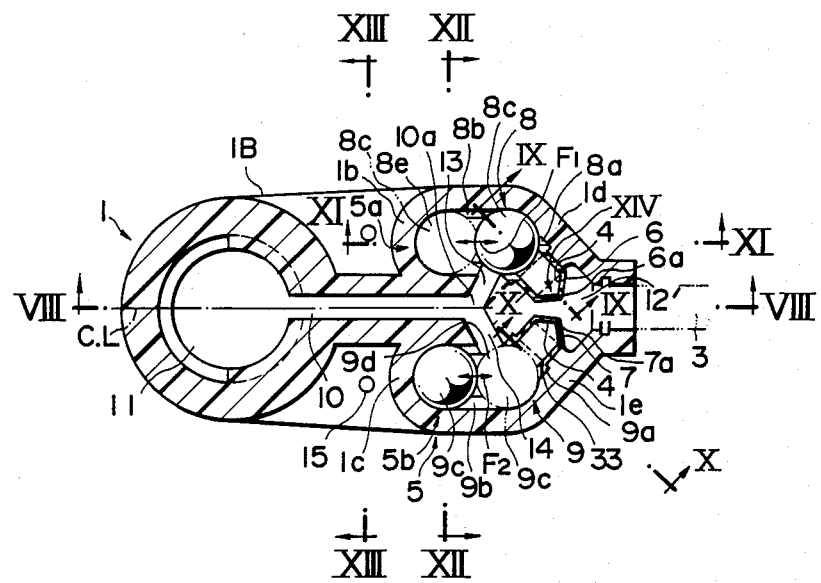
FIG. 7 is a sectional view of a second embodiment of the present invention showing a brain ventricle shunt taken along a line VII—VII of FIG. 8.
Figure 9:
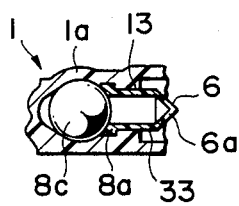
FIG. 9 is a sectional view taken along a line IX—IX of FIG. 7.
Figure 10:
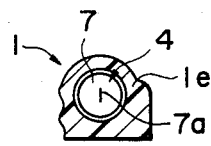
FIG. 10 is a sectional view taken along a line X—X of FIG. 7.
Figure 8:
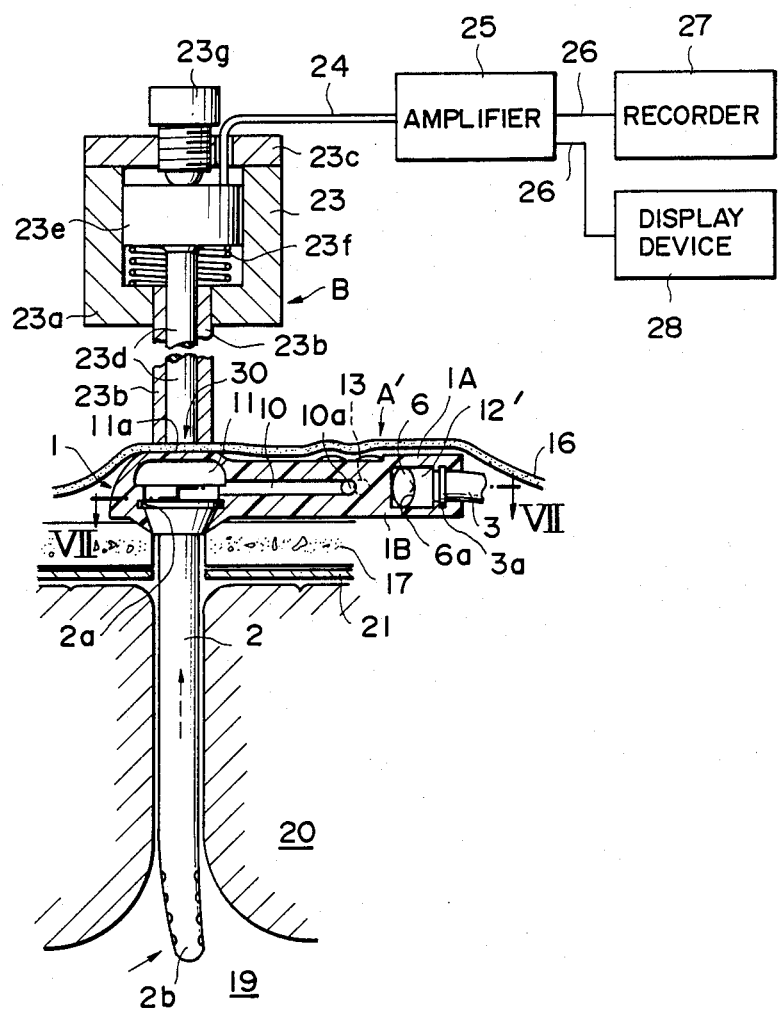
FIG. 8 is a sectional view of a brain ventricle shunt system of the second embodiment taken along a line VIII—VIII of FIG. 7.

Referring to FIG. 7, the flow-rate switching mechanism comprises a first flow-rate switching part 5a provided with the slit-type relief valve 6 and ball-type ON-OFF valve 8 which are both interposed in the first flow passage 13 in order to control the flow rate to the predetermined flow rate $Q_1$, as well as a second flow-rate switching part 5b provided with the slit-type relief valve 7 and ball-type ON-OFF valve 9 which are both interposed in the second flow passage 14 in order to control the flow rate to the predetermined flow rate $Q_2$ ($=1/2Q_1$). The flow-rate switching mechanism 5 is also constructed in such a manner that the moving direction $F_1$, $F_2$ of the valve plugs 8c, 9c in these ON-OFF valves 8, 9 are parallel to each other and extend parallel to a center axis C.L of the shunt main body 1.

The ball-type ON-OFF valves 8, 9 are so disposed that axial lines of the both valves intersect on the center line C.L. In dependence on the disposition, the shunt main body has a pair of soft wall 1d, 1e along the valves 8, 9.

It will be understood that the flow-rate switching mechanism 5 also serves as a shut-off valve V by closing the first and second flow-rate switching parts 5a, 5b.

In operation, for measuring the pressure in the brain ventricle, the following procedure (0) is performed before the above described procedure (1) to (6) in the first embodiment.

Figure 2:
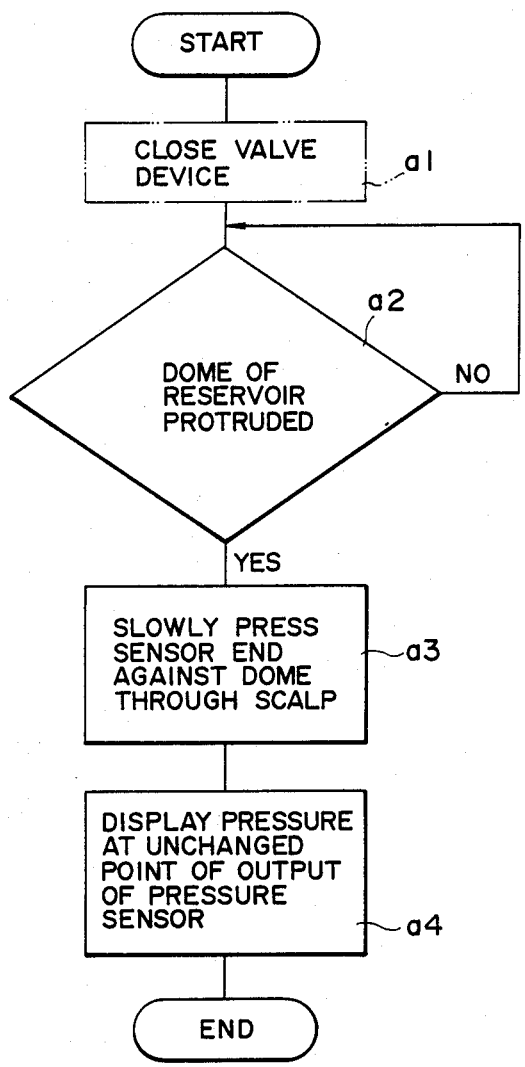
FIG. 2 is a flow chart showing pressure measuring operations.

(0) the shut-off valve V is closed to shut off the flow of cerebrospinal fluid from the peritoneum catheter 3 to the brain ventricle catheter 2 (step a1 of FIG. 2).

The system of the second embodiment has substantially the same operation and advantages as the first embodiment. The system further has a flow switching function as described hereinafter.

Figure 11A:
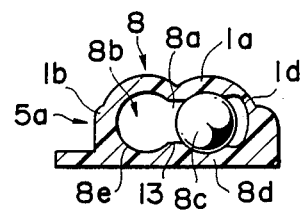
FIG. 11(a) is a sectional view taken along a line XI—XI of FIG. 7.
Figure 11B:
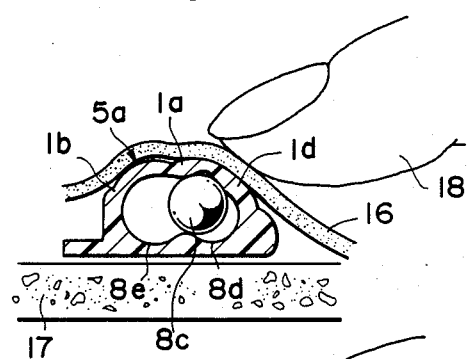
FIGS. 11(b) to 11(d) are sectional views of a ball valve showing the operation thereof.
Figure 11C:
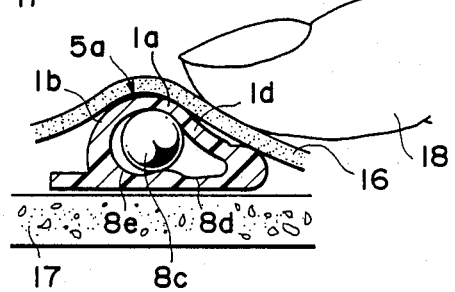
Figure 11D:
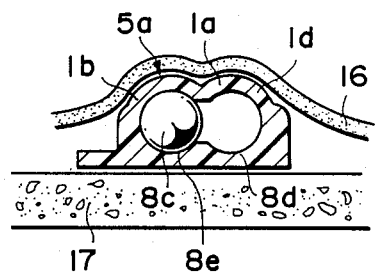
Figure 12:
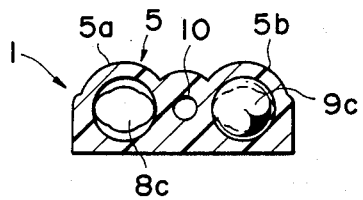
FIG. 12 is a sectional view taken along a line XII—XII of FIG. 7.
Figure 13:
FIG. 13 is a sectional view taken along a line XIII—XIII of FIG. 7.

As shown in FIG. 11(d), when movable spherical valve plugs 8c, 9c are positioned on the corresponding open-position holding hemispherical seats 8e, 9e, the cerebrospinal fluid which has flowed into the reservoir 11 from the brain ventricle of a patient by way of the brain ventricle catheter 2 passes through the main flow passage 10 and first and second flow passages 13, 14 into the valve chambers 8b, 9b and then flows further through the two ON-OFF valves 8, 9, each of which is in its open state, to positions upstream of the relief valves 6, 7.

If there is a difference greater than a predetermined value between the pressure of the cerebrospinal fluid on the upstream side of the relief valves 6, 7 and that of the cerebrospinal fluid of the downstream side of the relief valves 6, 7 at this time, the relief valves 6, 7 are maintained in their open state so that the cerebrospinal fluid flows out into the small compartment 12'. Further, the cerebrospinal fluid in the small compartment 12' flows into the peritoneum of the patient or into the auricle of the patient by way of the peritoneum catheter 3.

In the manner described above, the cerebrospinal fluid from the brain ventricle is allowed to flow at a maximum flow rate, which is the sum $(Q_1+Q_2)$ of the regulated flow rates of the two relief valves 6, 7.

When it is desired to change the flow rate to an intermediate flow rate $Q_1$, it is necessary to have the movable spherical valve plug 8c seated on the hemispherical seat 8e so as to maintain the first ON-OFF valve 8 open and at the same time to have the movable spherical valve plug 9c seated on the hemispherical seat 9d so as to close the second ON-OFF valve 9 as shown by the phantom lines in FIG. 7. In this manner, the cerebrospinal fluid is allowed to flow only through the first relief valve 6 having the relatively large regulated flow rate.

When it is desired to change the flow rate to a still smaller flow rate $Q_2$, it is necessary to have the movable spherical valve plug 8c seated on the hemispherical seat 8d so as to close the first ON-OFF valve 8 and at the same time to have the movable spherical valve plug 9c seated on the hemispherical seat 9e so as to maintain the second ON-OFF valve 9 open as indicated by the solid lines in FIG. 7. In this manner, the cerebrospinal fluid is allowed to flow only through the second relief valve 7 having the relatively small regulated flow rate.

Since the first and second relief valves 6, 7 have different regulated flow rates in this embodiment as described above, the flow rate can be switched between three different levels by means of the two relief valves 6, 7. Even when both relief valves 6, 7 have the same regulated flow rate, the flow rate can be switched over between two different levels, namely, by causing the cerebrospinal fluid to flow through either one of the valves 6, 7 or through both of the valves 6, 7.

When it is desired to stop the drainage of the cerebrospinal fluid through the brain ventricle shunt, it is necessary to guide the movable spherical valve plugs 8c, 9c to their corresponding closed position holding hemispherical seats 8d, 9d so as to close both the first and second ON-OFF valves 8, 9, and thereby shut off the flow of the cerebrospinal fluid from the reservoir 11 through the main flow passage 10 and first and second branch flow passages 13, 14 to the relief valves 6, 7.

As shown in FIGS. 11(a) to 11(d), it is necessary to press the soft upper wall 1a by means of the finger 18 through the scalp 16 when it is desired to move the valve plugs 8c, 9c from the closed position holding hemispherical seats 8d, 9d toward the opened position holding hemispherical seats 8e, 9e.

When it is desired to move the valve plugs 8c, 9c from the opened position holding hemispherical seats 8e, 9e, toward the closed position holding hemispherical seats 8d, 9d, it is necessary to press the soft upper wall 1a and soft front walls 1b, 1c by means of the finger 18 through the scalp 16.

Since the moving directions $F_1$, $F_2$ of the valve plugs 8c, 9c are designed to be parallel to each other, it is easy to determine visually or palpably whether the ON-OFF valves 8, 9 are open or closed.

Figure 15:
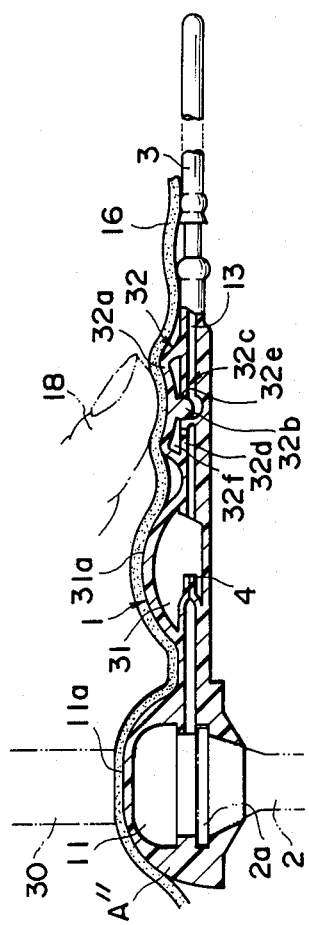
FIG. 15 is a sectional view showing a third embodiment of the present invention.
Figure 16:
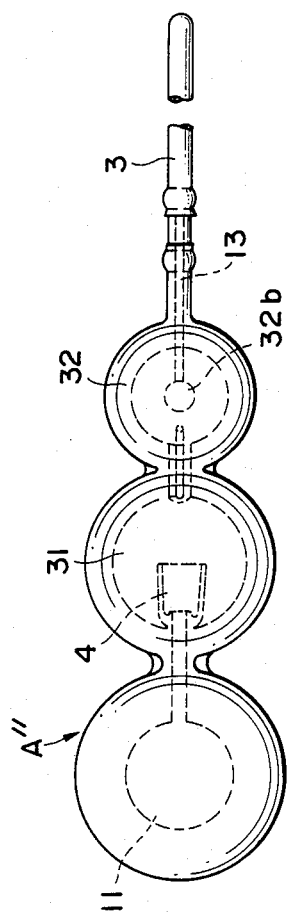
FIG. 16 is a plan view of the third embodiment of FIG. 15.
Figure 17:
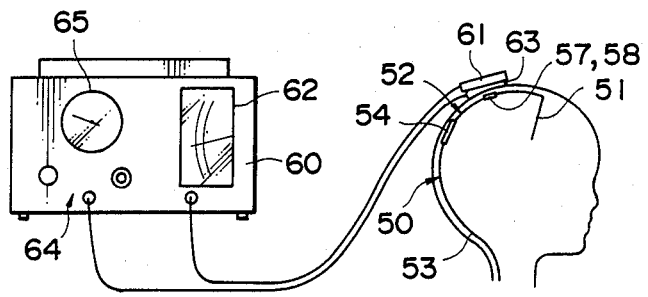
FIG. 17 is a schematic illustration of a conventional system for measuring pressure in the brain ventricle.
Figure 18:
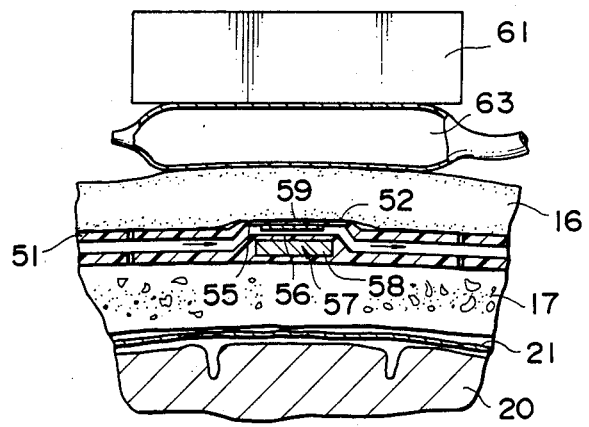
FIG. 18 is an enlarged sectional view showing a detecting portion of a brain ventricle shunt for the conventional system.

Referring to FIGS. 15 and 16 showing a third embodiment of the present invention, the reservoir 11 is communicated with the catheter 3 through the passage 13 in the shunt main body 1 of a brain ventricle shunt A''. A pump chamber 31 is formed adjacent the reservoir 11 and a plug valve 32 as a shut-off valve mechanism V is formed in the passage 13 adjacent the pump chamber 31. The pump chamber 31 has the check valve 4 in the form of a miter valve which is connected to the reservoir 11. The valve 32 has a dome-shaped flexible wall 32a, an internal cavity 32f defined by the flexible wall 32a and formed in the passage 13, a port 32e of the cavity communicated with the catheter 3, a valve seat 32c formed around the port 32e in an intermediate diaphragm 32d, and a plug 32b for closing the port 32e. The plug 32b is formed on the inside of flexible wall 32a so as to be moved along the valving axis toward and away from the valve seat 32c.

Other structures are the same as the previous embodiments. Accordingly, the pressure in the brain ventricle can be measured by the same operation as the aforementioned procedure (0) to (6) in the second embodiment, and the same advantages as the previous embodiments can be gained.

Describing the operation of the shut-off valve mechanism V, when the valve 32 is to be closed, the finger 18 presses down on the top of the flexible wall 32a through the scalp 16 as shown in FIG. 15. The plug 32b is forced into the valve seat 32c to close the port 32e.

To open the valve 32, a flexible wall 31a of the pump chamber 31 is pressed. The chamber 31 is compressed to a lesser volume, so that the check valve 4 closes to trap the fluid. Thus, the fluid is fed to the cavity 32f of the valve 32. The pressure is exerted on the flexible wall 32a to raise the plug 32b, pulling the valve seat 32c with the plug and opening the port 32e.

In the second and third embodiments, it is possible to provide three or more flow-rate switching parts in which the regulated flow rate of each switching part is set at a different level from each other. If the flow-rate switching parts are successively provided with regulated flow rates set, for example, at $Q \times 2^n$, the flow rate can be switched at $(2^n - 1)$ levels, in which Q is a minimum flow rate and n is a natural number.

Further, orifices having different flow rates may be arranged instead of relief valves 6, 7. Here, check valves may be interposed in the first and second flow passages 13, 14 or a single check valve may be interposed in the main flow passage 10.

The first and second flow-rate switching parts 5a, 5b may be constructed in such a way that the moving directions $F_1$, $F_2$ of the valve plugs 8c, 9c extend at right angles with respect to the central axis C.L of the shunt main body 1.

Further, the valve chambers 8b, 9b and small compartments 12' may be arranged in a vertical relationship.

In accordance with the present invention, the following advantages may be obtained.

(1) It is not necessary to carry out zero point adjustment (calibration) of pressure for the measurement of the pressure in the brain ventricle after the implantation of the shunt system.

(2) It is possible to provide the shunt system so as not to interfere with forming of a tomogram by the CT scanner, neuclear magnetic resonance scanner, and others.

(3) The system can be easily operated and has no injurious influences upon the brain when in the nonoperative state.

(4) The implantation operation can be easily done.

(5) The system can be installed at low cost.

While the invention has been described in conjunction with preferred specific embodiments thereof, it will be understood that this description is intended to illustrate and not limit the scope of the invention, which is defined by the following claims.

What is claimed is:

1. A system for measuring the pressure of cerebrospinal fluid in a brain ventricle of a patient, comprising:
   first means implantable beneath the scalp of a patient and extending into a brain ventricle of the patient for receiving therein cerebrospinal fluid under pressure from the brain ventricle, the first means having means defining a reservoir for receiving the cerebrospinal fluid, the reservoir having flexible portion which expands outwardly when the reservoir is filled with the cerebrospinal fluid; and
   second means for exerting, through the patient's scalp, an inward force on the reservoir flexible portion of a magnitude sufficient to flexibility compress the reservoir flexible portion inwardly a predetermined extent and for measuring the pressure of the cerebrospinal fluid in the brain ventricle according to the magnitude of the inward force.

2. A system according to claim 1, wherein the reservoir flexible portion is configured to have an arcuate shape when the reservoir is filled with cerebrospinal fluid; and the second means includes means for exerting an inward force of a magnitude sufficient to indent the arcuately-shaped flexible portion a predetermined extent.

3. A system according to claim 2; wherein the means for exerting an inward force includes a displaceable rod engageable with the patient's scalp in the region above the reservoir flexible portion, the rod having a generally flat end face effective to first flatten and then indent the reservoir flexible portion as the rod is displaced and pressed against the patient's scalp.

4. A system according to claim 3; including means including a discharge flow passage in fluid communication with the reservoir for discharging the cerebrospinal fluid from the reservoir to another location in the patient.

5. A system according to claim 4; including valving means for selectively valving closed the discharge flow passage so that cerebrospinal fluid remains stored in the reservoir to enable measurement of the cerebrospinal fluid pressure, and valving open the discharge flow passage so that cerebrospinal fluid flows therethrough to enable drainage of cerebrospinal fluid from the brain ventricle.

6. A system according to claim 5; wherein the valving means comprises at least one manually actuated ball valve displaceable to open and closed positions for opening and closing the discharge flow passage.

7. A system according to claim 5; wherein the valving means includes means for regulating the flow of cerebrospinal fluid at one of a plurality of selectable flow rates.

8. A system according to claim 1; including means including a discharge flow passage in fluid communication with the reservoir for discharging the cerebrospinal fluid from the reservoir to another location in the patient.

9. A system according to claim 8; including valving means for selectively valving closed the discharge flow passage so that cerebrospinal fluid remains stored in the reservoir to enable measurement of the cerebrospinal fluid pressure, and valving open the discharge flow passage so that cerebrospinal fluid flows therethrough to enable drainage of cerebrospinal fluid from the brain ventricle.

10. A system according to claim 9; wherein the valving means comprises at least one manually actuated ball valve displaceable to open and closed positions for opening and closing the discharge flow passage.

11. A system according to claim 9; wherein the valving means includes means for regulating the flow of cerebrospinal fluid at one of a plurality of selectable flow rates.

* * * * *